United States Patent [19]

Sting

[11] Patent Number: 5,093,580
[45] Date of Patent: Mar. 3, 1992

[54] ATR OBJECTIVE AND METHOD FOR SAMPLE ANALYZATION USING AN ATR CRYSTAL

[75] Inventor: Donald W. Sting, New Canaan, Conn.

[73] Assignee: Spectra-Tech, Inc., Stamford, Conn.

[21] Appl. No.: 622,852

[22] Filed: Dec. 6, 1990

Related U.S. Application Data

[63] Continuation-in-part of Ser. No. 487,550, Mar. 2, 1990, Pat. No. 5,019,715.

[51] Int. Cl.$^5$ .......................................... G01N 21/86
[52] U.S. Cl. .................................... 250/571; 250/216; 356/445
[58] Field of Search .................. 250/216, 237 G, 571, 250/572; 356/317–319, 445–448, 244

[56] References Cited

U.S. PATENT DOCUMENTS

| | | | |
|---|---|---|---|
| 3,393,603 | 7/1968 | Harrick | 88/14 |
| 3,958,882 | 5/1976 | Gast | 356/445 |
| 3,963,354 | 6/1976 | Feldman et al. | 356/168 |
| 4,062,623 | 12/1977 | Suzuki et al. | 350/91 |
| 4,176,964 | 12/1979 | Knör et al. | 356/444 |
| 4,602,869 | 7/1986 | Harrick | 346/244 |
| 4,657,390 | 4/1987 | Doyle | 356/244 |
| 4,812,041 | 3/1989 | Doyle | 356/244 |
| 4,878,747 | 11/1989 | Sting et al. | 350/511 |
| 5,019,715 | 5/1991 | Sting et al. | 250/571 |

OTHER PUBLICATIONS

Nanosampling Internal Reflection Spectroscopy of Solids and Liquids by F. DeBlase, Spectroscopy, Jun. 1988, pp. 96–107.

Primary Examiner—David C. Nelms
Assistant Examiner—S. Allen
Attorney, Agent, or Firm—Calfee, Halter & Griswold

[57] ABSTRACT

An optical system, apparatus and method includes a visible energy source and a radiant energy source, means to direct visible or radiant energy at preselected but variable angles of incidence through an ATR crystal to a sample at a sample plane and means to collect encoded radiant energy reflected or emitted from the sample through the ATR crystal to a detector at preselected but variable angles of reflection or emission. The optical system, apparatus and method may further include a lens or other optical element selectively positioned in the optical path to change the focus of the optical path to initially survey the sample on a movable stage at a focal plane spaced from the sample plane. The survey mode permits easy identification of a surface area of interest on the sample to permit that area of interest to be moved into contact with a surface of the ATR crystal at the sample plane for subsequent accurate analysis thereof. The optical system, apparatus and method may have three modes of operation (namely a survey mode, a viewing mode or an analysis mode) passing visible or radiant energy to and from a sample or reference material through an ATR crystal.

17 Claims, 8 Drawing Sheets

ATR OBJECTIVE AND METHOD FOR SAMPLE ANALYZATION USING AN ATR CRYSTAL

CROSS-REFERENCE TO RELATED APPLICATION

The present application is a continuation-in-part of copending and co-owned application Ser. No. 487,550, filed on Mar. 2, 1990, now U.S. Pat. No. 5,019,715, and entitled "Optical System and Method for Sample Analyzation".

FIELD OF THE INVENTION

The present invention relates, in general, to an optical system and method and, in particular, to an optical system and method utilizing an ATR apparatus.

BACKGROUND OF THE INVENTION

Crystals utilizing total internal reflection or attenuated total reflection (ATR) principles are well known in optical systems for analyzing samples by determining the optical constants thereof and by establishing the physical and chemical composition thereof. Examples of ATR crystals in various optical systems are shown, for example, in U.S. Pat. Nos. 4,602,869 and 3,393,603. These ATR crystal optical systems utilize rather complicated optical paths, which limit the flexibility of those systems and limit the type and size of sample that can be analyzed.

An example of such an ATR crystal system is disclosed in an article appearing in the June, 1988 issue of the Spectroscopy magazine. A nano-sampler, apparently offered by Harrick Scientific Corporation, is pictured and described in that article. As pictured, an internal reflection crystal has a fibrous sample positioned against part of a sampling surface. A mask is selectively positioned at, or very near, the sample plane to allow selected energy reflected from the sample to escape from the crystal and pass through the output side of the optical system to a detector. A visible light viewing system is positioned above the sampling surface apparently to allow the sample, sample surface and sample plane to be observed to assist in positioning the sample and mask at the sample plane. The ATR crystal is set up in this optical system to act like a light pipe in directing energy therealong to the angularly positioned sample surface at one end thereof. The Harrick optical system is rather complicated and does not allow any visible light viewing through the ATR crystal to the sample.

SUMMARY OF THE INVENTION

The present invention provides an optical system, apparatus and method to utilize an ATR crystal in a microscope objective system. A flat or nearly flat surface of the ATR crystal is positioned in the sample plane of the optical system. The sample or reference material may be pressed against the flat crystal surface to maintain intimate contact therebetween. The optical system has three different operational modes: namely, a survey mode; a viewing mode and an analysis mode. In all three of these modes, the visible or radiant energy passes through the ATR crystal to reach the sample.

In the survey mode, an optical element, such as a refractive lens, is positioned in the optical path of the optical system to refract visible light passing therethrough. As thus refracted, the visible light passes through the ATR crystal and sample plane to a survey focus at a focal plane spaced from the sample plane. The sample is mounted on a conventional microscope stage and can be moved in the X and Y (or R and 0) directions in the focal plane to allow the analyst to easily survey the entire sample field. The surface area of analytic interest can be quickly identified in this survey mode and fixed in the X and Y directions at or immediately adjacent the survey focal point in the focal plane. The stage and sample can then be moved only in the Z direction to bring the surface area of interest on the sample into contact with the flat surface of the ATR crystal at the sample plane. The conventional microscope stage structure can be used to apply pressure to hold the sample surface of interest firmly against the flat ATR crystal surface at the "analysis" or operative focal point of the optical system in either the viewing or analysis modes.

In the viewing mode, the refractive lens or other survey-optical element is removed from the optical path and is replaced by optional inlet and outlet masks. The analyst can then view along that optical path through the inlet mask and ATR crystal to the sample area of interest in contact with the flat surface of the ATR crystal at the operative focal point of the optical system.

The angle of incidence to and the angle of emission or reflectance from the ATR crystal and sample can be selectively varied by apertures in the inlet and outlet masks positioned at or near a Fourier plane or a conjugate thereof. The inlet and outlet apertures may be selectively varied in size, shape, number and relative spacial locations according to the analytical study being performed. In the viewing mode, the analyst can look along the optical path through the mask aperture and ATR crystal to see the surface area of interest on the sample at the focal point on the sample plane. The masks can be changed to vary the analysis being made without moving the sample.

In the analysis mode, radiant energy passes along the optical path through the first or inlet mask, the inlet half of a reflecting microscope objective and the ATR crystal to the surface area of the sample. Some of the radiant energy is then reflected or emitted from the sample through the crystal, to thereafter pass through the outlet half of the reflecting microscope objective and second or outlet mask to a detector. This optical system allows analyzation of small samples using the ATR technique. In addition, the variable angles of incidence and reflection or emission allow for different studies to be performed providing variable depths of radiant energy penetration at the sample.

These and other objects and advantages of the present invention will become apparent as the following description proceeds.

DETAILED DESCRIPTION OF THE PREFERRED EMBODIMENT

Figure 1:
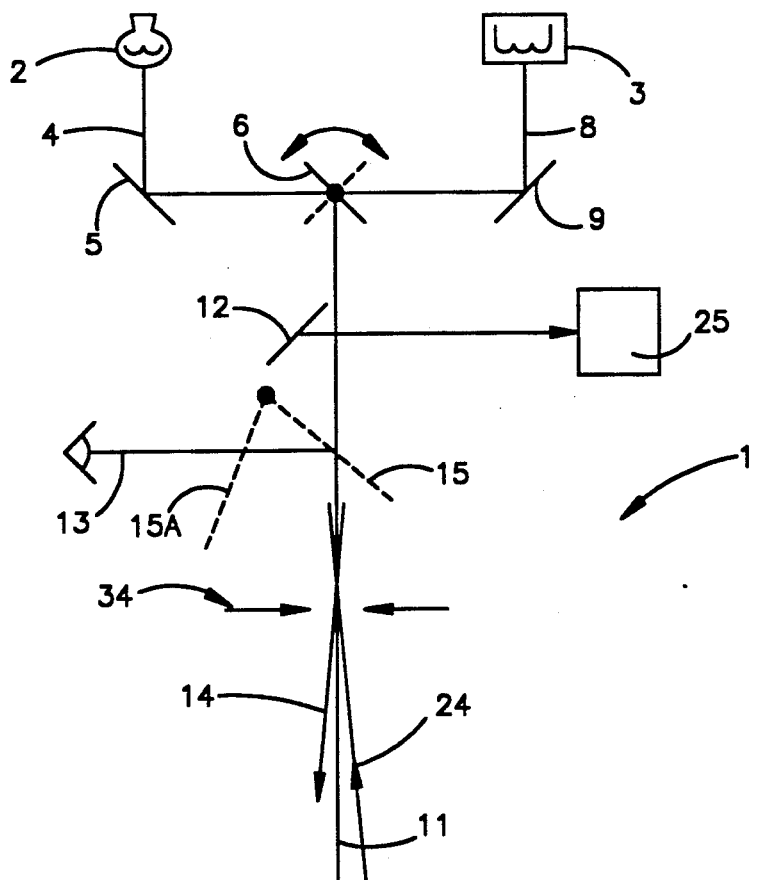
FIG. 1 is a schematic elevation of the optical system of the present invention set up in the viewing mode with the sample in contact with a surface of the ATR crystal at the sample plane.
Figure 1:
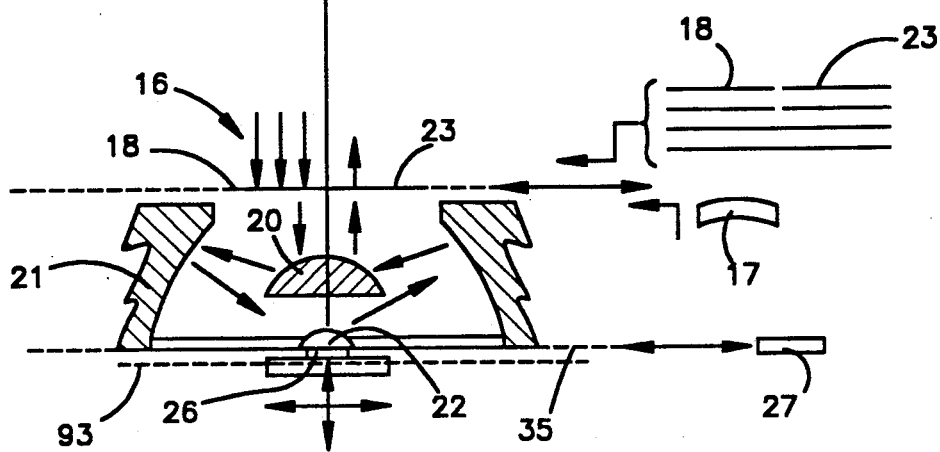

Turning now in more detail to the invention and initially to FIG. 1, the optical system and apparatus of the present invention is indicated generally at 1. The optical system includes a visible light source 2 and a radiant energy source 3. The term radiant energy, as used herein, means any wave band of energy, with mid-range infrared energy being used in the current embodiment.

The light source 2 emits a beam of visible light 4 reflected by mirror 5 to pivotal source switching mirror 6. In the full line position shown, mirror 6 reflects the visible light downwardly at a 90° angle along the optical path of the system.

The radiant energy source 3 selectively emits a beam 8 of radiant energy. The radiant energy beam 8 is reflected by mirror 9 toward source switching mirror 6. When pivoted to its dashed line position, source switching mirror 6 reflects the radiant energy at a 90° angle downwardly along the optical path of the system.

The optical path of the system is split in half along the optical centerline 11. For this purpose, a mirror 12 can be positioned at or adjacent an aperture image plane. The mirror 12 effectively blocks and discards all incoming visible energy 4 or radiant energy 8 on the left of the optical centerline 11 as viewed in FIG. 1. By thus splitting the incoming energy, the visible or radiant energy passing on the right toward the ATR objective moves as a half beam in the direction of arrow 14 along the left side of the optical centerline 11 as viewed in FIG. 1.

The optical system 1 of the present invention permits selective viewing of the inlet visible energy moving along the optical path. For this purpose, a pivotal beam splitter 15 is also positioned along the optical axis. In its position extending across the optical path, the beam splitter 15 permits a portion (approximately one-half) of the visible light 4 from visible energy source 2 to pass therethrough. The beam splitter 15 in such position also permits an analyst to look through a viewing port 13 and utilize the reflective portion of beam splitter 15 to view along the incoming energy path 14. In a radiant energy analysis mode, the beam splitter 15 is pivoted to a position removed from the optical path, as indicated by the reference numeral 15A.

The incoming visible or radiant energy passes through an ATR objective assembly, indicated generally at 16. The ATR objective assembly includes, on its input side, either an optical path changing element 17 or inlet mask 18, a secondary optic 20, a primary optic 21, and an ATR crystal 22. The ATR objective assembly, on its output side, includes the ATR crystal 22, the primary optic 21, the secondary optic 20 and either the optical path changing element or a second outlet mask 23. The primary optic 21 and secondary optic 20 are preferably mirrors cooperatively forming a reflecting objective, with the left half thereof as viewed in FIG. 1 being an inlet optic and the right half thereof being an outlet optic.

Energy leaving the ATR objective assembly 16 passes in the direction of arrow 24 from the right side of the centerline 11 of the optical system to the left side after imaging at the field stop 34. This energy leaving the ATR objective assembly is reflected off splitting mirror 12 to a detector 25. The detector 25 is used to optically analyze the sample material 26 or reference material 27 selectively positioned against a surface of ATR crystal 22 in the ATR objective assembly 16.

Figure 2:
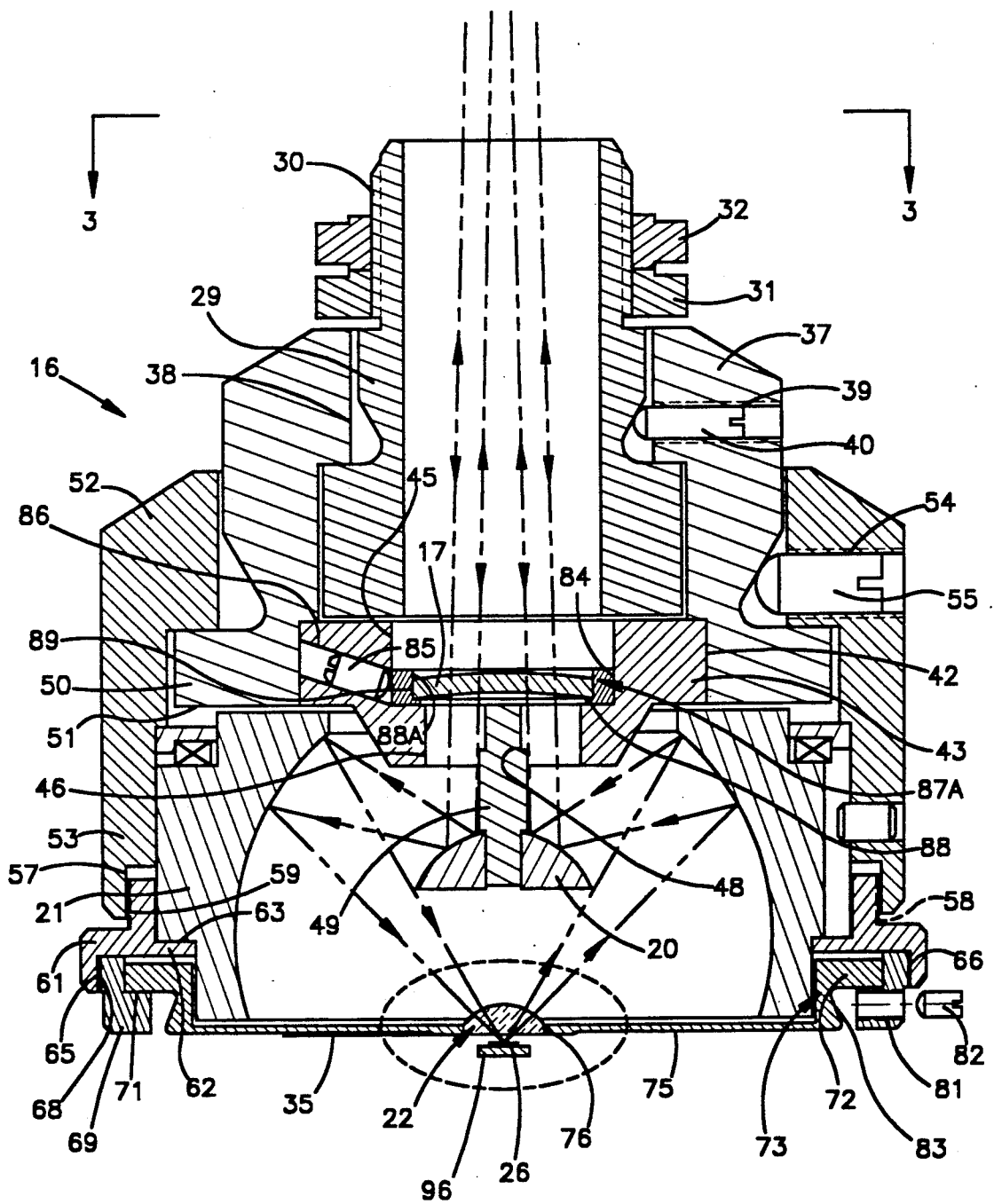
FIG. 2 is a vertical cross-section of the ATR crystal objective assembly according to one embodiment of the invention, shown in the survey mode with a refractive lens inserted in the optical path.

The ATR objective assembly 16 is best illustrated in FIG. 2. This ATR objective assembly may have many of the same structural elements as the objective assembly described in copending and co-owned U.S. Pat. application Ser. No. 487,550, which is incorporated herein by reference thereto. However, because of the many differences and additional features incorporated in the present invention, the entire objective assembly 16 is described for purposes of completeness.

The ATR objective assembly 16 includes a microscope connecting tube 29. The outer diameter of the connecting tube at its upper end is provided with threads 30. These threads mate with threads on one of the stations of a rotatable microscope nose piece. The connecting tube is threaded into the microscope nose piece station until properly positioned and held in place by jam nut 31 and lock nut 32. The visible and radiant energy of the optical system passes through the bore of the connecting tube 29. The jam and lock nuts properly position the ATR objective assembly 16 in the optical path of the microscope to establish the proper predetermined distance between the field stop of the optical system, indicated generally at 34 (FIG. 1), and the sample plane 35.

A guide holder 37 is positioned around and supported by connecting tube 29. A bore 38 through the guide holder body 37 receives the connecting tube 29. The guide holder 37 has a tapped hole 39 extending radially therethrough. A first optic centering screw 40 is threadedly received in tapped hole 39 and extends into contact at its inner rounded end with the outer diameter of connecting tube 29. By rotation, first centering screw 40 may be radially advanced or retracted relative to connecting tube 29 to provide some radial adjustment for the guide holder 37 relative to the centerline 11 of the optical system.

The bottom end of guide holder 37 has a bottom counterbore 42. This counterbore 42 receives a slide guide 43, which is fixedly secured thereto. The slide guide has a longitudinal slide slot 45 extending diametrically therethrough. A center bore 46 extends through the slide guide body, with such bore being concentric with the centerline 11 of the optical system to pass visible or radiant energy therethrough.

The secondary optic 20 is mounted to and suspended from the bottom of slide guide 43. For this purpose, mounting spider 48 extends diametrically across the center bore 46 of slide guide 43 and is connected to mounting pin 49 of secondary optic 20 to support that secondary optic in the optical path. By being diametrically oriented and properly positioned, the mounting spider 48 supports the secondary optic 20 in the optical path without significantly interfering with the effective input and output of visible or radiant energy to and from the ATR objective assembly 16. In this regard, the mounting spider 48 defines semi-circular openings on either side thereof consistent with the half beam shape of the inlet and outlet visible and radiant energy.

The bottom of guide holder 37 has a radially outwardly extending annular flange 50 thereon. The bottom wall 51 of flange 50 is horizontally aligned with the bottom surface of slot 45 to provide radial access to such slot. The flange 50 also provides support for a rotatable outer ring or collar 52.

The outer ring 52 includes a downwardly extending annular skirt 53, which has a threaded internal diameter. The primary optic 21 is received within annular skirt 53 on outer ring 52. The outer diameter of crystal mounting ring 61 has threads thereon to cooperate with the threads on the internal diameter of skirt 53. Therefore, rotation of the crystal mounting ring 61 will, depending upon direction of rotation, either raise or lower the primary optic 21 because the primary optic rests on ring 61. This elevational adjustment of the primary optic 21 may be used to obtain the proper spacial relationship between the primary optic and the secondary optic for proper optical alignment.

To provide further adjustment of the ATR objective assembly relative to the centerline of the optical path, outer ring 52 has a threaded hole 54 passing radially through its upper end. Threaded hole 54 receives a second primary optic centering screw 55. Radial advancement or withdrawal of second centering screw 55 can radially adjust the position of the outer ring 52 relative to the guide holder. This radial movement of outer ring 52 also radially adjusts the position of the primary optic 21 relative to the secondary optic 20 to obtain proper centering around the optical centerline 11 of the microscope.

A counter bore 57 is provided at the bottom end of annular skirt 53 of outer ring 52. The annular sidewall defined by counter bore 57 has internal threads 58 provided thereon. Threads 58 mate with external threads 59 on crystal mounting ring 61. The crystal mounting ring is threaded into outer ring 52 until its internal lip 62 engages a radially extending external shoulder 63 on primary optic 21. A downwardly extending collar 65 on ATR mounting ring 61 has its radially inner wall threaded, as shown at 66.

Threads 68 on the outer upper diameter of annular crystal mounting block 69 mate with threads 66 on the crystal ring 61 to allow the crystal mounting block 69 to be vertically adjusted relative to crystal mounting ring 61. The crystal mounting block 69 has an annular, radially inwardly extending shoulder 71 which supports a radially outwardly extending annular flange 72 on a crystal mounting pan, indicated generally at 73. The bottom wall 75 of crystal mounting pan 73 includes a center hole 76 receiving the ATR crystal, indicated generally at 22.

Figure 4:
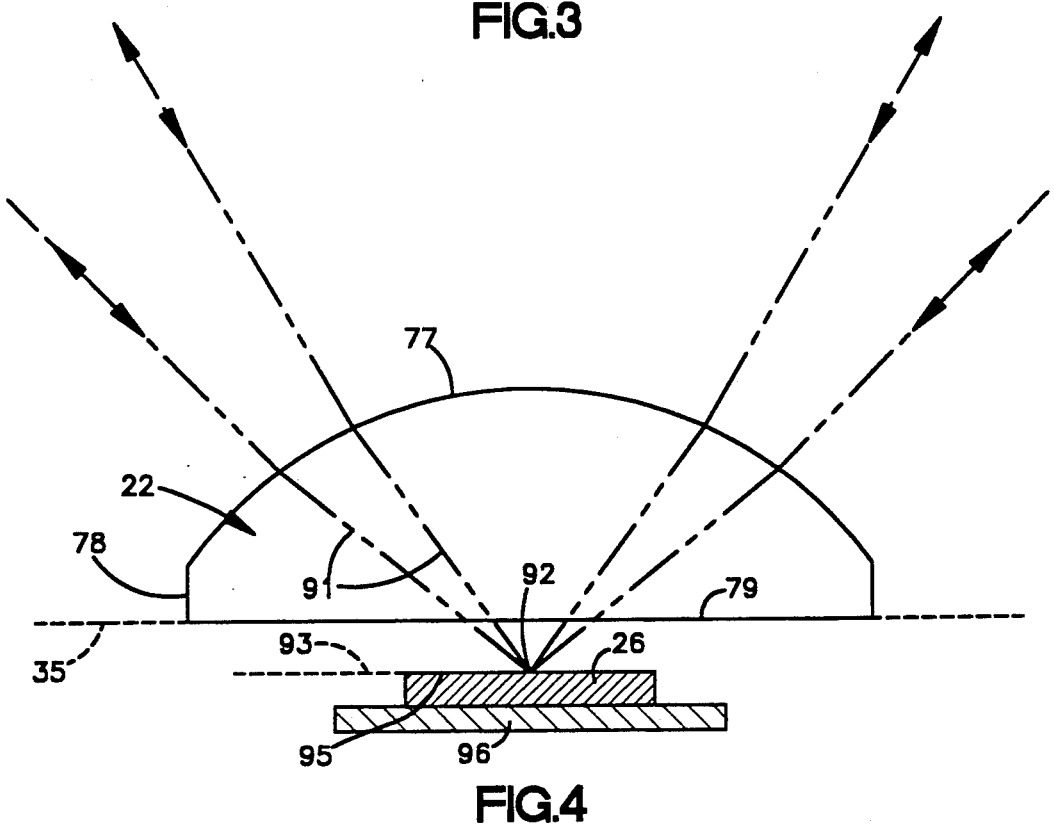
FIG. 4 is an enlargement of the ATR crystal, sample and sample stage from the circled area of FIG. 2 showing one surface of the sample positioned at a survey focal plane, which is spaced from the sample plane in the survey mode.

As best shown in FIG. 4, the ATR crystal 22 preferably includes a generally hemispherical upper surface 77, a generally cylindrical side wall 78 and a flat bottom wall 79. The ATR crystal 22 is secured in center hole 76 of the crystal mounting pan 73 in a position to locate the flat bottom wall 79 thereof flush with the lower surface of bottom wall 75. This ATR mounting pan 73 can also be vertically adjusted as necessary to position the bottom wall 79 of ATR crystal 22 in the sample plane 35. For this purpose, rotation of crystal mounting block 69 in one direction or the other will either raise or lower the mounting block 69 and crystal mounting pan 73 carried thereby relative to the crystal mounting ring 61. The mounting pan 73 is either raised or lowered until the bottom wall 79 of ATR crystal 22 lies in sample plane 35 of the optical system.

The crystal mounting pan 73 may also be radially adjusted to radially adjust the ATR crystal 22 carried thereby. For this purpose, mounting block 69 is provided with a tapped hole 81 passing radially therethrough. Threaded hole 81 receives a third optic centering screw 82. The inner rounded end of third centering screw 82 engages the outer sidewall surface 83 on crystal mounting pan 73. Radial advancement or withdrawal of the third centering screw 82 can radially adjust the position of the mounting pan 73 and ATR crystal 22 relative to the optical centerline 11 of the optical system. This selective radial adjustment of the ATR crystal permits the optical centerline 11 of the optical system to pass through the center of the crystal 22. The ATR crystal 22 is thus accurately positioned in the optical system for any of its operational modes.

Figure 3:
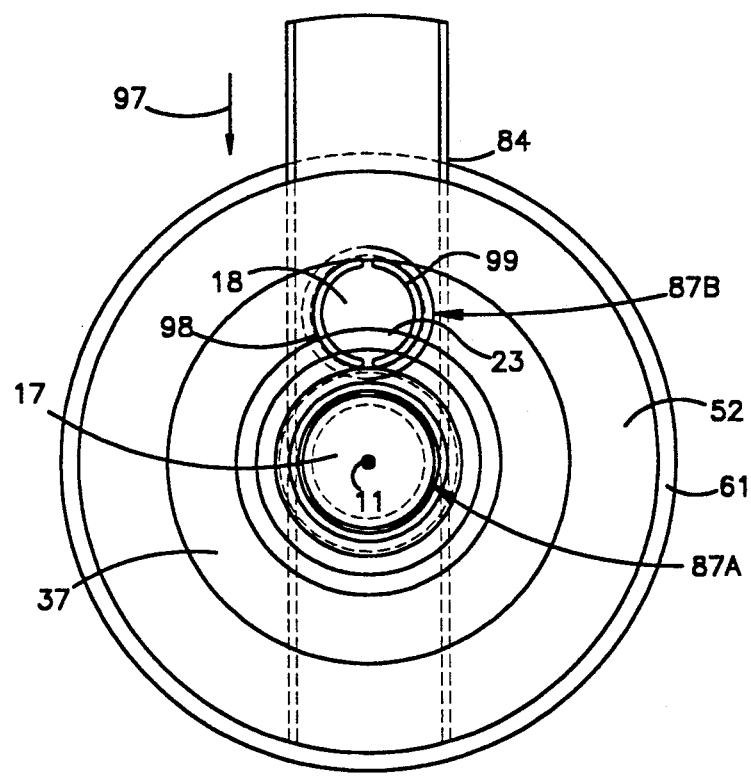
FIG. 3 is a plan view taken generally along the plane 3—3 of FIG. 2 showing the slide selectively located to position the refractive lens in the optical path for the survey mode.

For the survey mode, an optical element is inserted into the optical path to deflect or change its direction to create a focus thereof on a focal plane spaced from the sample plane. As shown in FIG. 2, the optical element may be a refractive lens 17 selectively slid into the optical path. For this purpose, a slide 84 may be radially inserted into and withdrawn from slot 45 in slide guide 43. The slide 84 has an elongated rectangular shape in plan view, as best shown in FIG. 3. The width of slide 84 substantially equals the width of guide slot 45 to provide a relatively tight sliding fit therebetween. In addition, some adjustment of the slide 84 may be provided by ball plunger 85 received in tapped hole 86 in slide guide 43. The inner rounded end of ball plunger 85 engages the side of slide 84. Rotation of ball plunger 85 in one direction or the other will advance or retract that plunger relative to slide guide 43 to correspondingly adjust the pressure on the slide 84 engaged thereby.

The slide 84 has two (or more) circular receptacles, indicated generally at 87A and 87B. As best shown in FIG. 2, each of these receptacles is defined by a bore 88 and counterbore 88A passing entirely through the slide 86. Each bore 88 and counterbore 88A cooperate to define a bottom lip 89 therebetween protruding slightly radially inwardly to provide support for the optical element and/or the inlet and outlet masks selectively positioned in receptacle 87A or 87B.

In the survey mode, the slide 84 is positioned to locate the refractive lens 17 in receptacle 87A in the optical path. With the lens thus positioned, the visible light passing through lens 17 reflects off the secondary optic 20 and main optic 21 and then passes through the ATR crystal 22 as schematically illustrated by lines 91 in FIG. 4. The visible light is focused at "survey" focal point 92 on focal plane 93. As shown, focal plane 93 is positioned below and spaced from sample plane 35.

Figure 7:
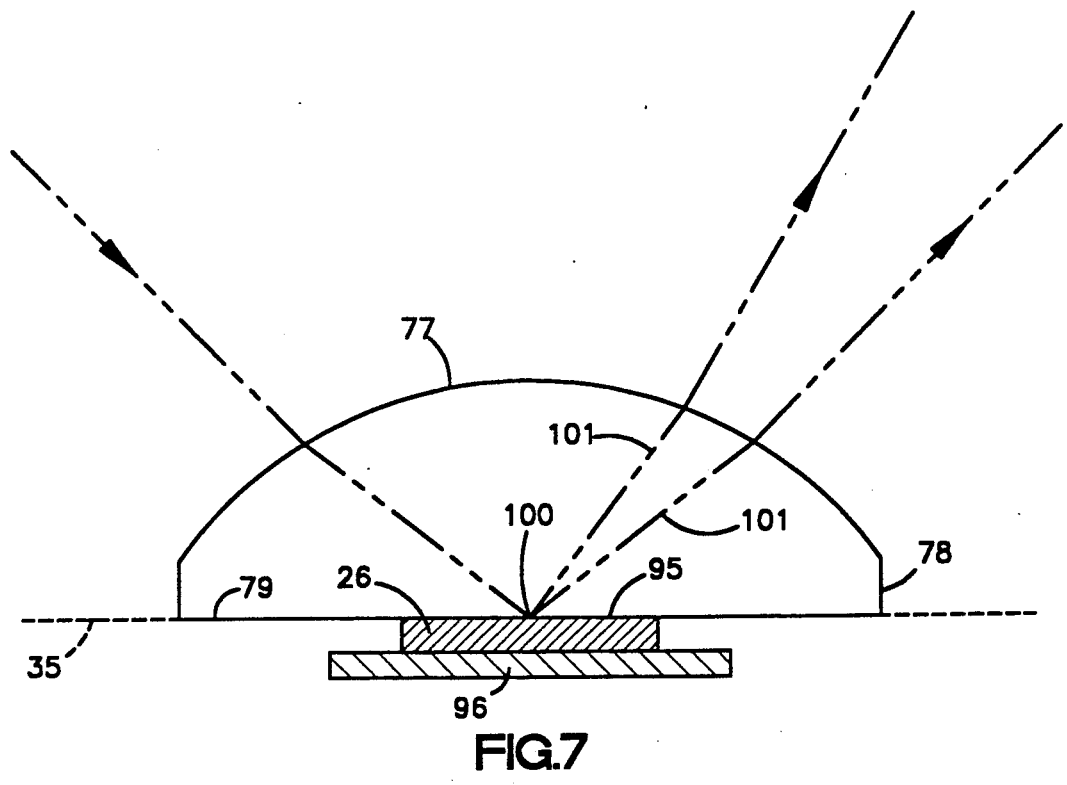
FIG. 7 is an enlargement of the ATR crystal, sample and sample stage from the circled area of FIG. 5 showing one surface of the sample held in contact with the bottom surface of the ATR crystal at the sample plane.

In the survey mode, one surface 95 of sample 26 is positioned to lie in focal plane 93. A conventional microscope stage 96 supports the sample 26 in such position and can be moved in the X and Y directions within the focal plane 93 to allow the analyst to survey the entire surface area 95 to identify an area of analytic interest. To perform that survey mode function, the analyst views along the optical path through the lens 17, reflecting objective and ATR crystal 22 to the sample surface 95 at focal plane 93. When an area of interest is identified, the X, Y position of the sample area of interest is fixed and the stage 96 is moved in only a Z direction to bring sample surface 95 into contact with flat bottom surface 79 of crystal 22, as shown in FIG. 7. The conventional stage 96 is used to apply pressure and clamp the sample 26 to the crystal 22 to provide intimate and continuous surface contact between sample surface 95 and flat crystal surface 79. This intimate surface contact enhances the accuracy and sensitivity of the objective assembly 16 in the viewing and sampling modes.

Figure 6:
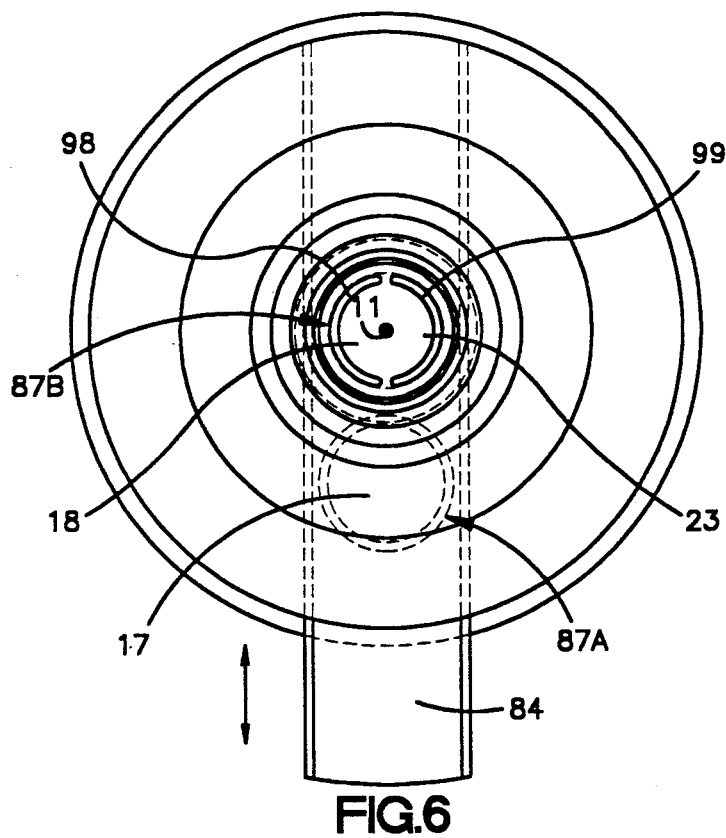
FIG. 6 is a plan view taken generally along the plane 6—6 of FIG. 5 showing the slide selectively located to position the inlet and outlet masks in the optical path.

For these modes, the slide 84 is indexed in the direction of arrow 97 in FIG. 3 to a second position in which receptacle 87B thereon is positioned in the optical path. This new position of slide 84 is illustrated in FIG. 6. Receptacle 87B selectively receives an inlet mask 18 and outlet mask 23, which may be integrally formed in a single disc (as shown in FIGS. 3 and 6) or in split discs as schematically shown in FIG. 1.

As illustrated, the inlet mask 18 has a semi-circular inlet aperture 98, and the second or outlet mask 23 has a semi-circular outlet aperture 99. Inlet aperture 98 and outlet aperture 99 have the same configuration and radius about the centerline 11 of the optical system and thus specular reflectance studies are performed with this mask arrangement on the sample being analyzed. In addition, as shown, the inlet aperture 98 and outlet aperture 99 are respectively adjacent the outer peripheries of inlet mask 18 and outlet mask 99 whereby the angles of incidence and collection will be at large angles of incidence relative to the sample 26.

The shape, number, size and radial position of the inlet and outlet apertures may be mixed and matched as desired for the specific analysis being made. Reference may be had to copending and co-owned U.S. Pat. application Ser. No. 487,550 for a more complete discussion of mixing and matching different apertures for different types of analyses.

With the inlet mask 18 and outlet mask 23 in the optical path as illustrated in FIG. 6, the optical system is set up for either the viewing mode or analysis mode. The masks are positioned at a Fourier plane of the optical system. For purposes of the present application, a Fourier plane is defined as a plane having the property that the radial position that a ray intersects that plane has a directly correlated function, normally linear, to the angle of incidence or reflection or emission that the ray will have with the sample plane after passing from or to the objective.

In the viewing mode, the analyst can see through viewing port 13 along the optical path through inlet aperture 98, Cassegrain objective and crystal 22 to the surface 95 of the sample 26 positioned at the sample plane. The analyst can thus see the targeted area of interest at the selected angle of incidence through the ATR crystal 22 at the operative focal point on the sample plane 35 prior to beginning analytic studies. This viewing allows the analyst to selectively observe and vary the experiments without moving the sample merely by changing the inlet and outlet apertures used to vary the angle of incidence and reflection or emission.

In the analysis mode, a narrow band of radiant energy from source 3 sequentially passes through aperture 98 in inlet mask 18, the reflecting objective and crystal 22 to the sample 96. With the preferred ATR crystal shown, the radiant energy will bounce or reflect off the sample 26 only one time. Some amount of radiant energy will be absorbed by the sample depending upon the material making up the sample. The remainder of the energy will be reflected off and/or emitted from sample 26 through the ATR crystal into the reflecting objective as indicated by the lines 101 in FIG. 7.

This reflected or emitted energy leaving ATR crystal 22 reflects off the primary optic 21 and secondary optic 20 and then passes through outlet aperture 99 in second mask 23 on its way to the detector 25. The outlet aperture 99 thus collects a certain selected band of reflected or emitted radiant energy for analysis and blocks all remaining reflected or emitted radiant energy on the outlet side of ATR objective assembly 16.

The outlet radiant energy reaching the detector 25 is encoded with information about the sample 26 because of the energy absorbed by the sample at the selected angle of incidence and reflection. The sample material 26 can thus be analyzed utilizing ATR principles on small samples or on small areas of interest on a specific sample by passing radiant energy through and from an ATR crystal.

Although the operation of the optical system and apparatus of the present invention is believed apparent from the above, a brief description of the optical system 1 shown in FIGS. through 7 is described below for purposes of completeness. Initially, to set up for the survey mode, the switching mirror 6 is pivoted to its full line position shown in FIG. 1, the beam splitter 15 is positioned across the optical path, the refractive lens 17 is positioned in the optical path, and the top surface 95 of sample 26 or reference material 27 is positioned in focal plane 93. The visible light source 2 is then turned on and the analyst views through sight tube 13.

Figure 5:
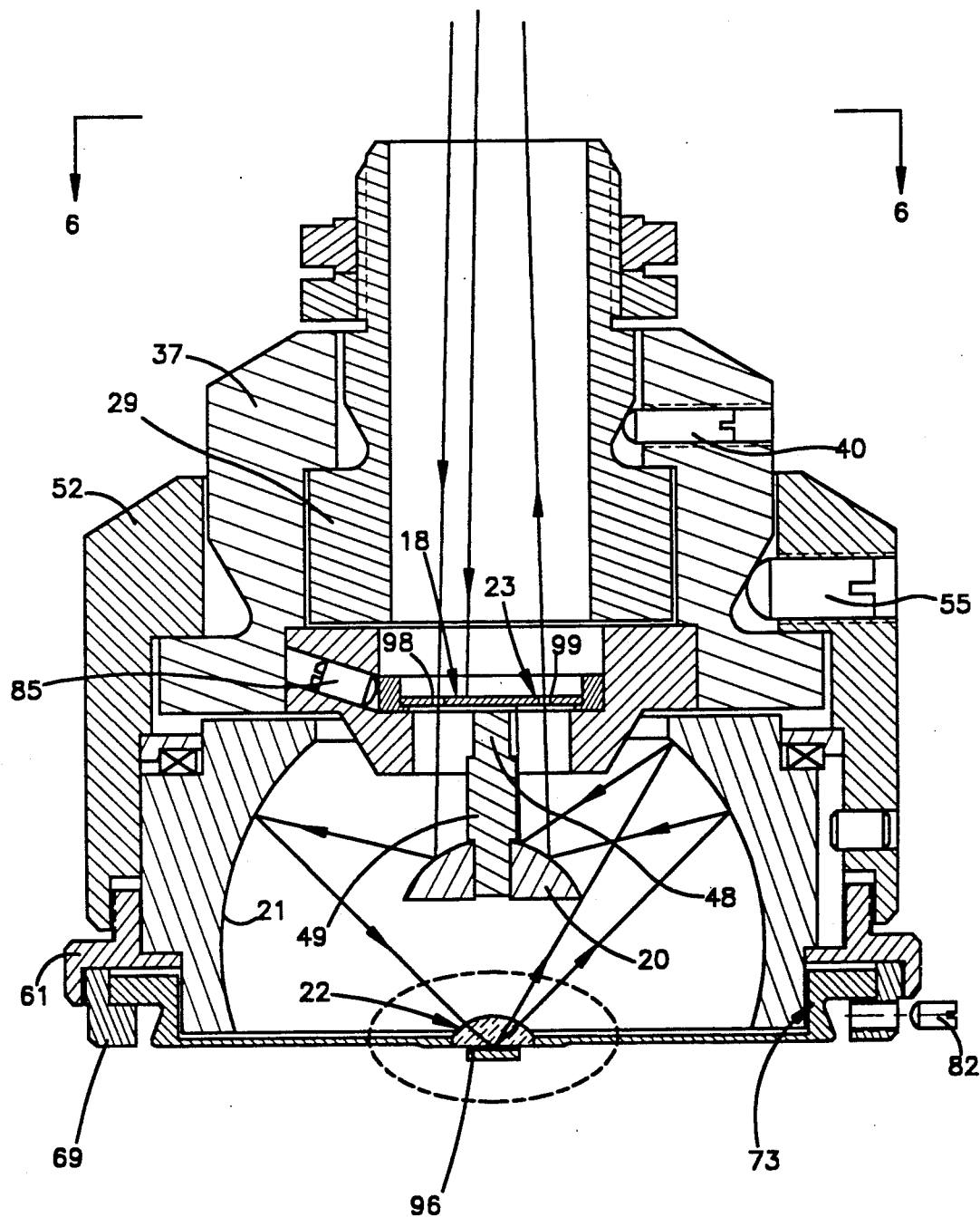
FIG. 5 is a vertical cross-section of the ATR objective assembly similar to FIG. 2, but showing the viewing or analysis modes of the ATR objective assembly with the sample being held against the ATR crystal and the inlet and outlet masks being positioned at the Fourier plane.

In the survey mode, the analyst sees through the refractive lens 17, reflecting objective and ATR crystal to the surface 95 of sample 26 lying in the focal plane 93. The spectroscopist can manipulate the microscope stage controls to move the stage 96 and thus sample 26 in the X and Y directions. This two directional movement in the focal plane allows the entire sample surface 95 to be easily surveyed to easily identify an area of analytic interest thereon. The sample is then fixed in the X and Y directions and the stage 96 moved in the Z direction to bring sample surface 95 into intimate, pressed contact with bottom surface 79 on crystal 22, as shown in FIGS. 5 and 7.

The optical system may then be converted to the viewing mode by indexing slide 84 in the direction of arrow 97 to locate receptacle 87B in the optical path. Inlet mask 18 and outlet mask 23, received in receptacle 87B, respectively have inlet and outlet apertures therein for the analytic study selected. By thus indexing the slide, the inlet mask 18 and outlet mask 23 are positioned in the optical path.

The analyst can thus view the selected area of interest on the sample at the selected angle of incidence. Specifically, with visible light source 2 still on, the analyst views through aperture 98, the reflecting objective and ATR crystal 22 to the area of interest on surface 95 of sample 26 located at the focal point 100 on sample plane 35. At the completion of the viewing mode, the optical system is converted to the radiant energy analysis mode.

For this purpose, the switching mirror 6 is pivoted to its dotted line position of FIG. 1, the beam splitter 15 is pivoted out of the way to position 15A and the inlet and outlet masks remain in their respective positions in the optical path. Radiant energy source 3 is then available to emit a radiant energy beam 8 which passes along the optical path of the system.

Specifically, radiant energy moves in a direction of arrow 14 and sequentially passes through inlet aperture 98, reflecting objective and ATR crystal 22 to the surface area of interest on sample 26 located at focal point 100. Depending upon the sample being analyzed, the sample 26 will absorb some radiant energy and the remaining radiant energy will reflect or be emitted from the sample surface 95 and then pass through the ATR crystal as indicated by lines 101 in FIG. 7. The radiant energy leaving the ATR crystal 22 will reflect off the second half or side of the primary optic 21 and secondary optic 20. The radiant energy passing through outlet aperture 99 in outlet mask 23 will be collected and the rest will be blocked. The collected radiant energy passing through outlet aperture 99 reflects off splitting mirror 12 to detector 25 for analysis of the sample material as discussed above.

Other embodiments of this invention are possible as shown, for example, in FIGS. 8 through 11. This second embodiment includes many common elements to the first embodiment, with such common elements being identified by the same reference numerals.

In the second embodiment, the stem 49A supporting secondary optic 20 has a bore 105 passing therethrough. Bore 105 communicates at its bottom end with a bore 106, passing through secondary optic 20. A refractive lens 17A is positioned in the bore 106, as best shown in FIG. 8.

For the survey mode utilizing refractive lens 17A, a lens mask 108 is positioned in receptacle 87A of slide 84. The survey mask 108 has a central aperture or hole 109 having a diameter equal to or slightly smaller than the diameters of bore 105 in stem 49A and bore 106 in secondary optic 20. In the survey mode, hole 109 is centered on optical centerline 11 and is thus in vertical alignment with bores 105 and 106.

Figure 8:
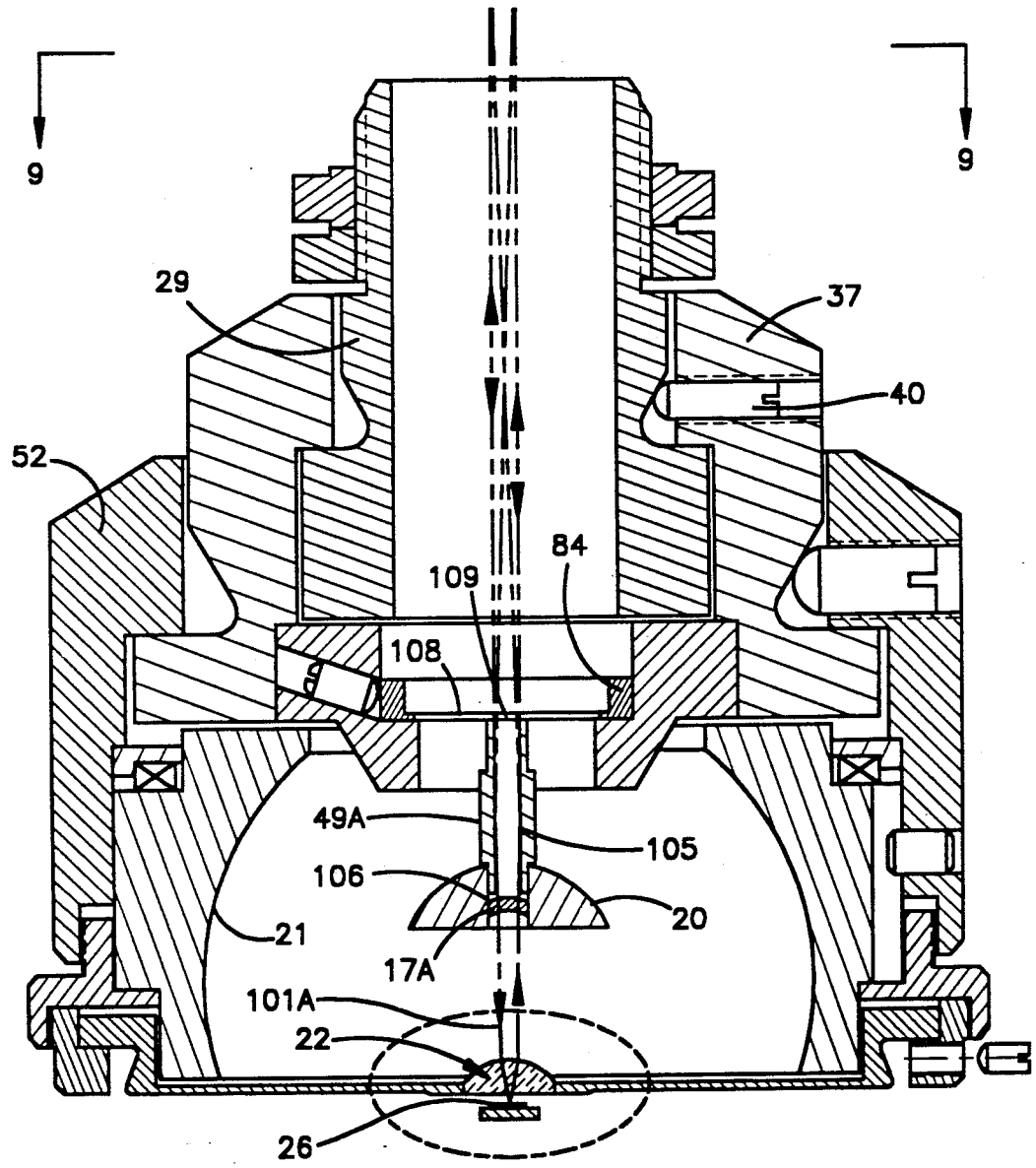
FIG. 8 is a vertical cross-section of an ATR objective assembly according to a second embodiment of the present invention shown in the survey mode with a refractive survey lens positioned in a central bore in the secondary optic of the Cassegrain objective.
Figure 9:
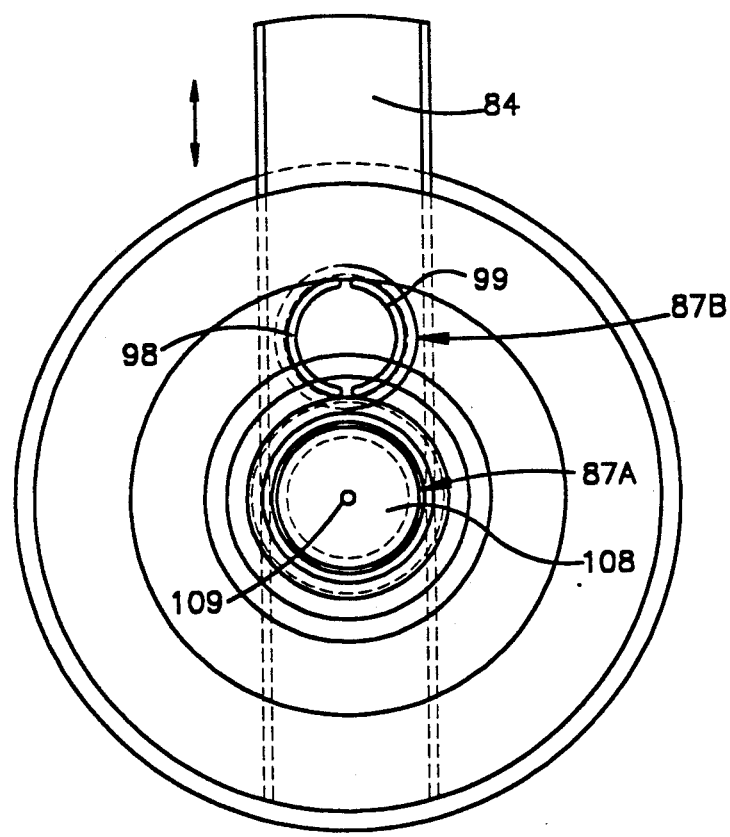
FIG. 9 is a plan view of the ATR objective assembly taken generally along the plane 9—9 of FIG. 8 showing the slide selectively located to position a lens mask in the optical path to direct visible light through the central bore of the secondary optic.
Figure 10:
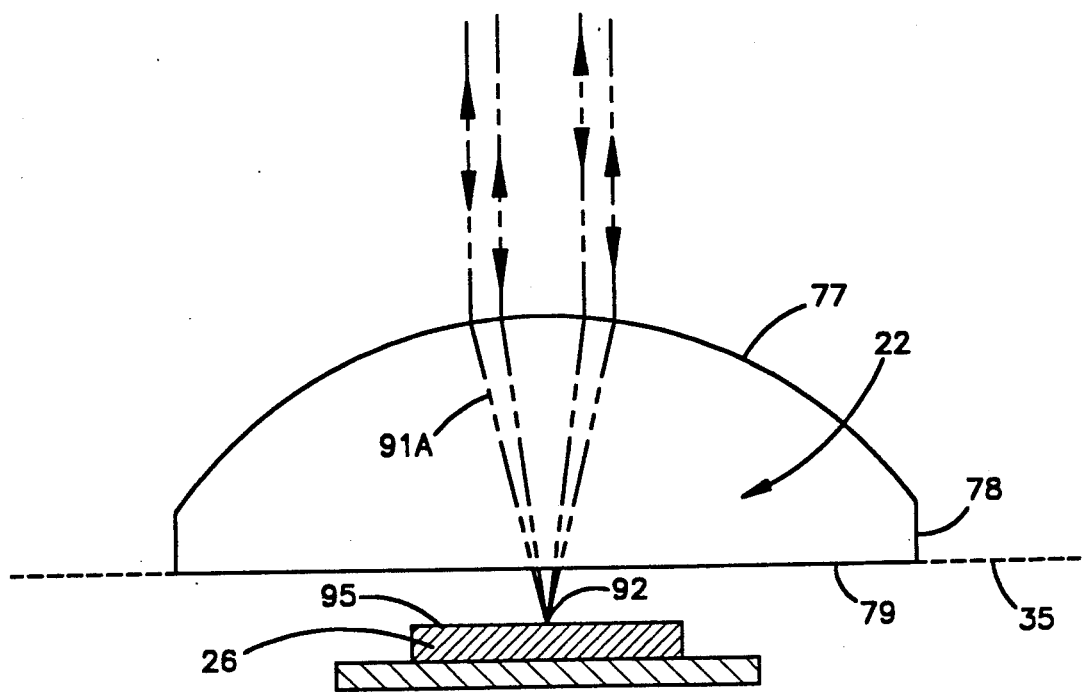
FIG. 10 is an enlarged vertical elevation of the ATR crystal, sample and sample stage of the second embodiment in the survey mode with the upper surface of the sample being positioned in a focal plane spaced from the sample plane.
Figure 11:
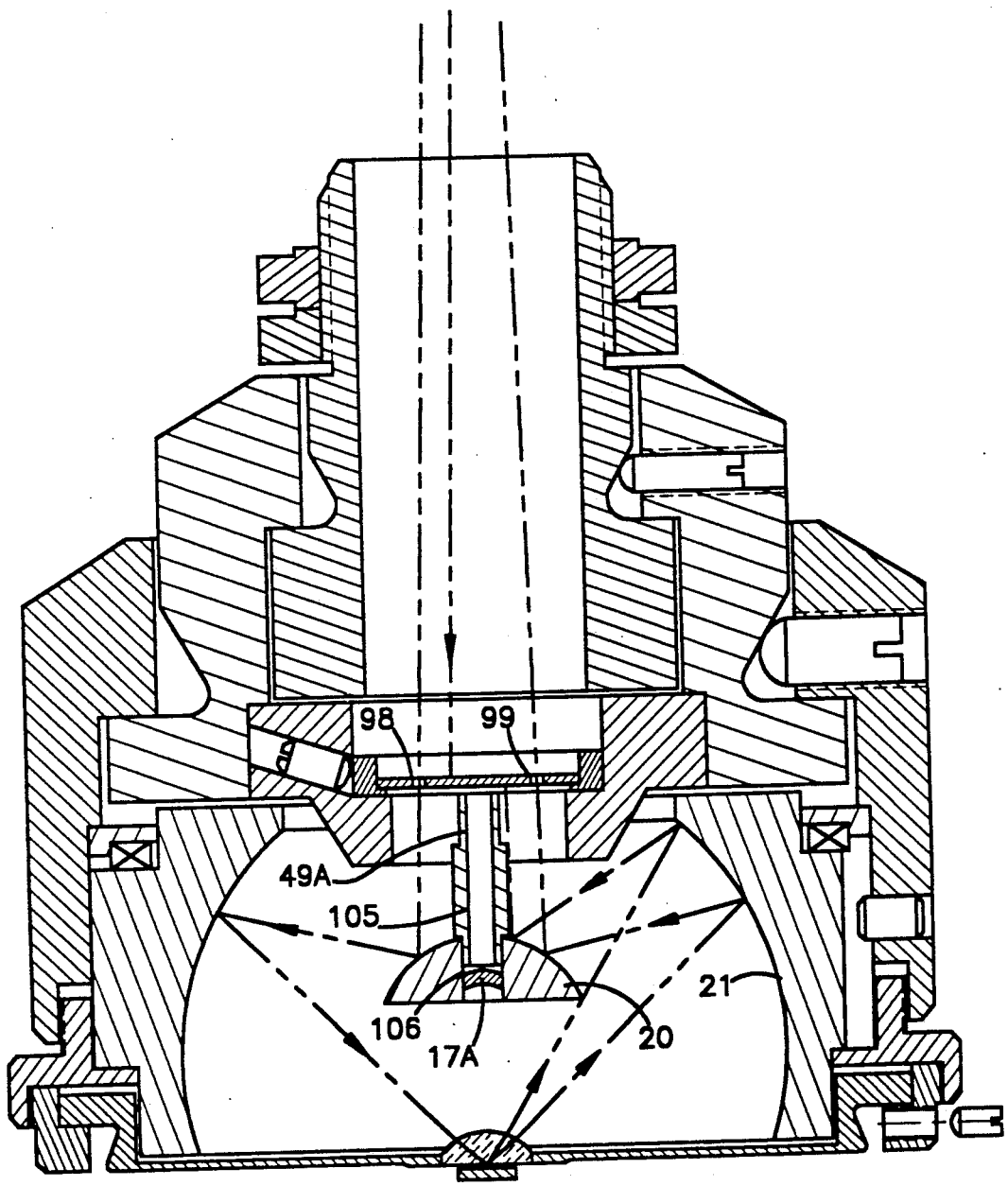
FIG. 11 is a vertical section of the ATR objective assembly of the second embodiment shown in FIG. 8 illustrating the sample positioned in contact with the bottom surface of the ATR crystal and the apertured inlet and outlet masks positioned in the optical path for either the viewing or analysis modes.

When slide 84 is located in its first position, survey lens mask 108 is positioned in the optical path for the survey mode, as illustrated in FIGS. 8 and 9. Visible light from visible energy source 2 will sequentially pass through hole 109, bore 105, bore 106, refractive lens 17A and crystal 22 in reaching surface 95 of sample 26 at the focal plane 93. The analyst uses this visible light path schematically identified as 91A in FIG. 8 and 10 for the survey mode described above. For the viewing mode or analysis mode, the slide 86 is indexed to its second position locating the inlet mask 18 and outlet mask 23 in the optical path as described above. The viewing and analysis modes of the second embodiment operate as described above and are illustrated in FIG. 11, with the inlet and outlet masks so positioned.

It will be apparent from the foregoing that changes may be made in the details of construction and configuration without departing from the spirit of the invention as defined in the following claims. For example, the optical path changing element 17 may be any type of optical element inserted in the optical path at any position therealong operative to focus visible light at a focal plane spaced from the sample plane. Furthermore, different ATR crystals can be utilized having different shapes and different operational and optical characteristics, such as multiple bounce or reflection features.

I claim:

1. An optical system for analyzing a sample or reference material comprising:
   a source of radiant energy selectively emitting radiant energy along an optical path of the optical system;
   a source of visible energy selectively emitting visible light along the optical path;
   a sample plane having an ATR crystal mounted therein;
   means for selectively positioning the sample or reference material at the sample plane in contact with one surface of said ATR crystal;
   means in the optical path for directing and concentrating either visible light or radiant energy through the ATR crystal to the sample plane;
   means using visible light to selectively view in a viewing mode along the optical path through the ATR crystal to the sample or reference material positioned at that sample plane; and
   means for collecting and detecting radiant energy that has passed through the ATR crystal and been encoded by the sample or reference material in contact therewith to allow analyzation of the sample or reference material in an analysis mode by using the encoded radiation collected and detected.

2. The optical system of claim 1 wherein the ATR crystal has a substantially hemispherical entrance surface and a flat surface in contact with the sample or reference material, with the visible and radiant energy passing through the crystal reflecting off the sample or reference material in contact therewith only once.

3. The optical system of claim 1 wherein the means for directing and concentrating includes first mask means removably positioned at approximately a Fourier plane or conjugate thereof to the sample plane or conjugate thereof to selectively allow only certain visible or radiant energy to pass therethrough to target that energy at preselected variable angles of incidence to the ATR crystal and sample plane.

4. The optical system of claim 3 wherein the means to collect and detect includes a second mask means removably positioned at approximately a Fourier plane or conjugate thereof to the sample plane or conjugate thereof to selectively allow only certain radiant energy reflected or emitted from the sample to pass therethrough at selected variable angles.

5. The optical system of claim 4 wherein the first and second masks include apertures therein which may be mixed and matched as desired for the types of analysis studies being performed.

6. The optical system of claim 5 wherein the means for directing and concentrating includes one half of a mirror objective system positioned between the first mask and sample plane and the means to collect and detect includes the other half of the mirror objective system positioned between the sample plane and second mask.

7. The optical system of claim 6 further including optical path changing means inserted in the optical path to result in the visible light that passes through the ATR crystal being focused at a focal plane spaced from the sample plane to allow the sample or reference material to be visibly surveyed in a survey mode to select an area of interest, the means for positioning can then be moved to place the area of interest into contact with the ATR crystal for subsequent radiant or visual energy analysis.

8. The optical system of claim 7 wherein the optical path changing means includes an optical element to deflect the visible light passing therethrough to create a focal point at the focal plane.

9. The optical system of claim 7 wherein the optical path changing means includes a lens positioned in a bore in a secondary optic of the Cassegrain objective and further includes a third mask selectively positioned in the optical path to direct visible light through said bore and said lens positioned in said bore to refocus the optical path at said focal plane.

10. The optical system of claim 8 wherein the first and second masks are removably mounted at a first position on a slide and a refractive lens is removably mounted as the optical element at a second position on the slide spaced from said first position on a slide, whereby said slide may be moved relative to the optical path alternately to position the refractive lens in the optical path for the survey mode or to position the first and second masks in the optical path for either the viewing mode or analysis mode.

11. The optical system of claim 1 further including optical path changing means inserted in the optical path to result in the visible light that passes through the ATR crystal being focused at a focal plane spaced from the sample plane to allow the sample or reference material to be visibly surveyed in a survey mode to select an area of interest which can then be moved into contact with the ATR crystal for radiant energy analysis.

12. The optical system of claim 1 wherein the means for collecting and detecting includes a mask means to selectively allow only certain encoded radiant energy or visible energy to pass therethrough toward a detector.

13. A method of analyzing a sample or reference material comprising the steps of:
a. masking an optical path at approximately a Fourier plane or conjugate thereof to a sample plane or conjugate thereof with mask means having apertures therein (1) to selectively direct visible or radiant energy through an ATR crystal at a preselected but variable angle of incidence to a sample or reference material selectively in contact therewith at a sample plane and (2) to selectively collect energy emitted from said ATR crystal and sample or reference material at a preselected but variable angle of reflection or emission;
b. viewing the sample or reference material in a viewing mode with visible light passing through the masking means and ATR crystal to the sample or reference material; and
c. analyzing the sample or reference material in an analysis mode by detecting encoded radiant energy which has been reflected off or emitted from the sample or reference material and passed through the ATR crystal and masking means.

14. The method of claim 13 including the further step of selectively varying the direction of the optical path to pass visible light through the ATR crystal and sample plane to a focal plane positioned therebelow. path to pass visible light through the ATR crystal and sample plane to a focal plane positioned therebelow.

15. The method of claim 14 including the further steps of viewing the sample or reference material temporarily positioned in the focal plane in a survey mode to identify and position an area of interest on the sample or reference material at a focal point on that focal plane and thereafter moving that area of interest into contact with an ATR crystal surface at the sample plane.

16. A method of analyzing a sample or reference material in an optical system comprising the steps of:
(a) initially viewing with visible light through an ATR crystal to a sample positioned at a focal plane spaced from said ATR crystal;
(b) initially moving the sample in the focal plane to identify an area of interest on a surface of that sample;
(c) moving the area of interest of the sample into contact with a surface of the ATR crystal at or adjacent a focal point on a sample plane;
(d) viewing with visible light through the ATR crystal to the sample at the sample plane to observe the area of interest at a selected angle of incidence; and
(e) analyzing the sample (1) by passing radiant energy through the ATR crystal to the sample, and (2) by selectively collecting radiant energy reflected or emitted from the sample for analysis at a detector.

17. The method of claim 16 including the further step of (f) varying the angles of incidence to and reflection or emission from the sample by masking with apertures selectively having various sizes, numbers, shapes and positions which can be mixed and matched depending upon the analysis being done.

* * * * *